US00PP33393P2

(12) United States Plant Patent
Van Swieten

(10) Patent No.: US PP33,393 P2
(45) Date of Patent: Aug. 24, 2021

(54) ***PHALAENOPSIS* ORCHID PLANT NAMED 'PHALWALWHO'**

(50) Latin Name: ***Phalaenopsis* hybrid**
Varietal Denomination: PHALWALWHO

(71) Applicant: ANTHURA B.V., Bleiswijk (NL)

(72) Inventor: Martinus Nicolaas Gerardus Van Swieten, Utrecht (NL)

(73) Assignee: Anthura B.V., Bleiswijk (NL)

( * ) Notice: Subject to any disclaimer, the term of this patent is extended or adjusted under 35 U.S.C. 154(b) by 0 days.

(21) Appl. No.: 17/300,108

(22) Filed: Mar. 10, 2021

(51) Int. Cl.
*A01H 5/02* (2018.01)
*A01H 6/62* (2018.01)

(52) U.S. Cl.
USPC ..... Plt./311
CPC ..... *A01H 6/62* (2018.05)

(58) Field of Classification Search
USPC ..... Plt./311
CPC ..... A01H 6/62
See application file for complete search history.

(56) References Cited

PUBLICATIONS

UPOV hit on a *Phalaenopsis* plant named, 'PHALWALWHO', QZ PBR 2019/2066, filed Aug. 30, 2019.*

* cited by examiner

*Primary Examiner* — Anne Marie Grunberg
(74) *Attorney, Agent, or Firm* — Jondle & Associates, P.C.

(57) ABSTRACT

A new and distinct variety of *Phalaenopsis* plant named 'PHALWALWHO', particularly characterized by light purple, shaded flowers with dark reddish-orange and yellow lips, a concave dorsal sepal shape in cross section, few branches, and is propagated by meristem tissue culture, is disclosed.

3 Drawing Sheets

Genus and species: *Phalaenopsis* hybrid.
Variety denomination: 'PHALWALWHO'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHALWALWHO'.

The new *Phalaenopsis* plant is a product of a planned breeding program conducted by the inventor in Bleiswijk, the Netherlands. The objective of this breeding program was to create a new, branched *Phalaenopsis* plant with attractive, light purple, shaded flowers with dark reddish-orange and yellow lips, suitable for potted plant production.

The new *Phalaenopsis* plant 'PHALWALWHO' is a result of cross-pollination made by the inventor in September 2010 in Bleiswijk, the Netherlands, of the proprietary female, or seed parent, *Phalaenopsis* hybrid '8543-01' (unpatented) with the proprietary male, or pollen parent, *Phalaenopsis* hybrid '20370-01' (unpatented).

The new *Phalaenopsis* was selected by the inventor as a single plant within the progeny of the stated cross-pollination in a controlled greenhouse in Bleiswijk, the Netherlands, in September 2013. Asexual reproduction of the new *Phalaenopsis* plant by meristem tissue culture since 2015 in Bleiswijk, the Netherlands, has demonstrated that the new variety reproduces true to type with all of the characteristics, as herein described, firmly fixed and retained through successive generations.

Community Plant Variety Rights for this variety have been applied for in the European Union on Aug. 30, 2019 (Application no. 2019/2066), by Applicant who obtained the subject matter disclosed directly from the inventor. 'PHALWALWHO' has not been made publicly available or sold anywhere in the world prior to the effective filing date of this application with the exception of sales or disclosures made one year or less before the effective filing date of this claimed invention by Applicant who obtained 'PHALWALWHO' directly from the inventor.

SUMMARY OF THE INVENTION

The following are the most outstanding and distinguishing characteristics of this new cultivar when grown under normal horticultural practices in Bleiswijk, the Netherlands, and can be used to distinguish 'PHALWALWHO' as a new and distinct variety of *Phalaenopsis* plant:

1) Light purple, shaded flowers with dark reddish-orange and yellow lips;
2) Dorsal sepal shape in cross section is concave; and
3) Plant has few branches.

DESCRIPTION OF THE PHOTOGRAPHS

This new *Phalaenopsis* plant is illustrated by the accompanying photographs which show the overall plant habit including blooms and foliage of the plant; the colors shown are as true as can be reasonably obtained by conventional photographic procedures. The photographs were taken in a greenhouse in Bleiswijk, the Netherlands, from 50-week-old plants in January 2021. Colors in the photographs may differ from the color values cited in the detailed botanical description, which accurately describe the actual colors of the new variety.

DESCRIPTION OF THE NEW VARIETY

Figure 1:
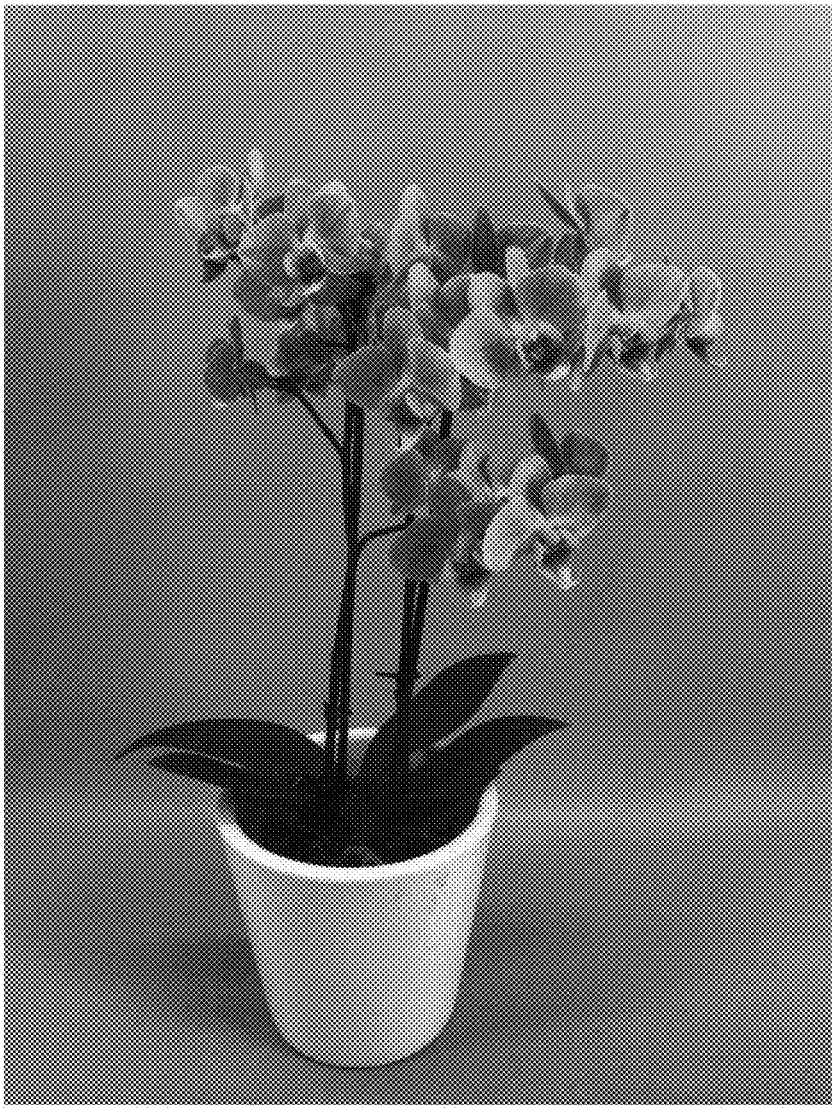
FIG. 1 shows the overall plant habit, including blooms and foliage of 'PHALWALWHO'.
Figure 2:
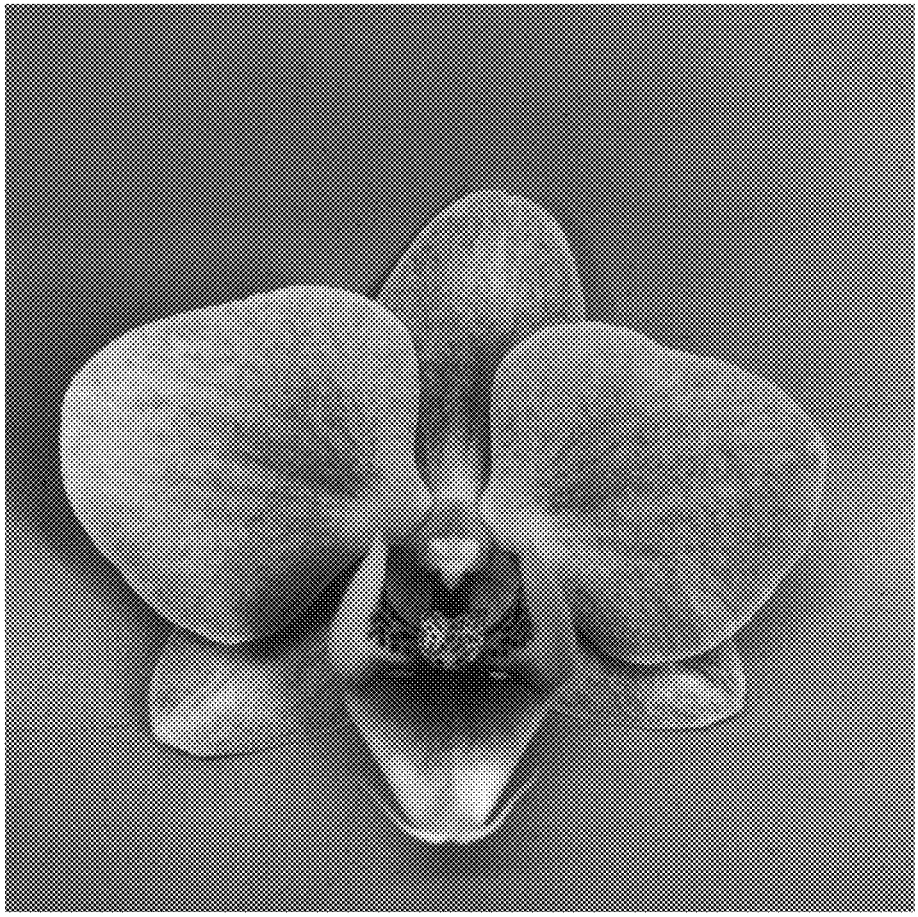
FIG. 2 shows a close-up of a flower of 'PHALWALWHO'.
Figure 3:
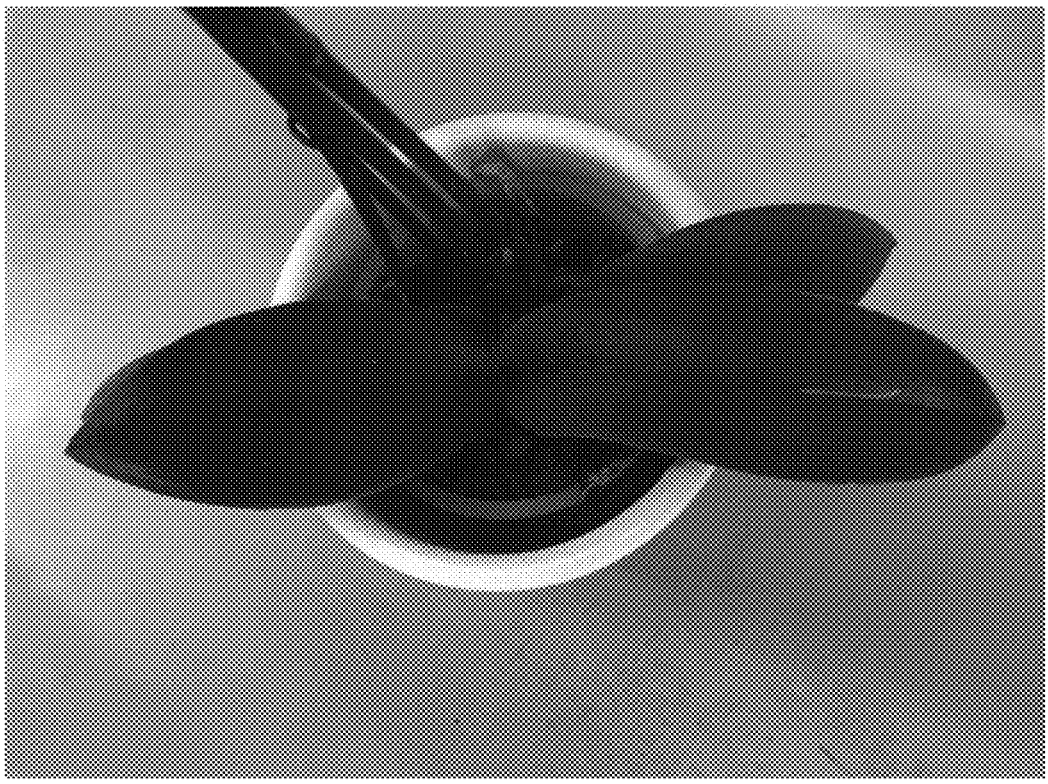
FIG. 3 shows an overhead view of the leaves of 'PHALWALWHO'.

The following detailed description sets forth the distinctive characteristics of 'PHALWALWHO'. Plants of the new *Phalaenopsis* have not been observed under all possible environmental conditions. The phenotype may vary somewhat with variations in environment such as temperature, light intensity, and day length, without, however, any variance in genotype. The chart used in the identification of colors described herein is The R.H.S. Colour Chart of The Royal Horticultural Society, London, England, 2015 edition, except where general color terms of ordinary significance are used. The color values were determined under 4000-6000 lux natural light in a greenhouse in Bleiswijk, the Netherlands. Observations and measurements were made in January 2021 on flowering plants which were planted in 12-centimeter (diameter) pots. After in vitro propagation, the plants were grown in nursery trays for 20-24 weeks, followed by transplantation to 12-centimeter pots and grown in a greenhouse between 27° C. to 29° C. for 30 weeks, continued by a cooling period of 8 weeks between 18° C. to 20° C. and 12 weeks in a greenhouse of 21° C. Flowering occurs after 50 weeks in 12-centimeter pots.

DETAILED BOTANICAL DESCRIPTION

Classification:

*Family*.—Orchidaceae.

*Botanical*.—*Phalaenopsis* hybrid.

*Common name*.—Moth orchid.

*Variety name*.—'PHALWALWHO'.

Parentage:

*Female parent*.—*Phalaenopsis* cultivar '8543-01' (unpatented).

*Male parent*.—*Phalaenopsis* cultivar '20370-01' (unpatented).

Propagation:

*Type*.—Meristem tissue culture.

Roots:

*Root description*.—Greyed-green (a color in between RHS 190B and RHS 190C) colored roots with branching lateral roots having yellow-green (RHS N144D) with a touch of dark pink (RHS 182C) colored root tips.

Plant:

*Crop time to flowering*.—Following asexual propagation (in vitro), the rooted cuttings grow for 20-24 weeks. After transplantation into 12-cm pots, the plants are finished after 48 to 50 weeks.

*Growth habit of the peduncle*.—Upright to slightly pendent with panicle inflorescence.

*Height (from soil level to top of inflorescence)*.—Approximately 32.0 cm to 37.0 cm.

*Width (measured from leaf tips)*.—About 26.0 cm to 28.0 cm.

*Vigor*.—Strong.

Leaves:

*Mature leaves*.—Quantity per plant: 7 to 8 leaves are produced before flowering. Length (fully expanded): 12.0 cm to 15.0 cm. Width: 5.0 cm to 6.0 cm. Position of the broadest part of the leaf: At the middle. Shape: Oblong. Base shape: Moderately elongated. Apex: Obtuse, slightly asymmetric. Leaf blade angle with the petiole (measured from the horizontal position): Between 15 degrees and 30 degrees. Leaf margin: Entire. Color: Upper surface: RHS 147A. Lower surface: RHS 146A with reddish-brown margin (RHS 200B). Texture (both upper and lower surfaces): Smooth. Thickness: 2.6 mm to 2.9 mm. Variegation: Absent. Venation: Pattern: Parallel. Color of the midvein: Upper surface: RHS 147A. Lower surface: RHS 200B.

Peduncle:

*Quantity per plant*.—1 to 3.

*Number of flowers per peduncle*.—13 to 16.

*Length*.—32.0 cm to 37.0 cm.

*Diameter*.—4.0 mm to 5.0 mm.

*Strength*.—Strong.

*Aspect*.—Upright to slightly pendent.

*Texture*.—Smooth.

*Color*.—Dark reddish-brown (RHS 200A) with a hint of light green (RHS 195A).

*Internode length*.—1.5 cm to 2.5 cm.

Inflorescence description:

*Appearance*.—Upright to slightly pendent, panicle inflorescence with bilaterally symmetrical flowers that open in succession beginning with the lowermost flower.

*Number of inflorescences*.—1 to 3.

*Inflorescence size*.—Height (from base to tip): 170.0 mm to 200.0 mm.

*Flowering time*.—First flowers can be expected 10 to 11 months after planting in a 12-cm pot.

*Flower*.—Height: 45.0 mm to 50.0 mm. Diameter: 55.0 mm to 60.0 mm. Depth of lip: 18.0 mm to 20.0 mm.

*Flower longevity*.—On the plant: 9 to 12 weeks.

*Flower shape*.—Flat.

*Fragrance*.—Absent.

*Flower bud*.—Average size: Medium. Length: 16.0 mm to 18.0 mm. Width: 14.0 mm to 16.0 mm. Color: Touch of yellow-green (RHS N144D) at the base; purplish-red (a color in between RHS N77B and RHS N79C).

*Petals*.—Arrangement: Open/free. Shape: Semi-circular. Apex: Obtuse asymmetric. Margin: Weakly undulated. Length (from base to tip): 26.0 mm to 28.0 mm. Width: 28.0 mm to 30.0 mm. Position of the broadest part of the petal: Toward the base. Color (when fully opened): Upper surface: Basic color: Light purple (RHS 76A). Over color: Purplish-pink shade (RHS N78D) and stripes (RHS N78C). Lower surface: Basic color: Light purple (RHS 76A). Over color: Touch of white (RHS NN155C) at the base toward margins; purplish-pink shade (RHS N78C). Number of spots and stripes on the petals (upper surface): Few stripes. Color of spots and stripes on the petals (upper surface): RHS N78C. Density of netting of the petals (upper surface): None. Color of the netting (upper surface): None.

*Dorsal sepal*.—Shape: Elliptic. Apex: Slightly emarginated symmetric. Margin: Entire. Length (from base to tip): 28.0 mm to 30.0 mm. Width: 17.0 mm to 19.0 mm. Position of the broadest part of the dorsal sepal: Toward the base. Color (when fully opened): Upper surface: Basic color: Light purple (RHS 76A). Over color: Light reddish-purple shade (RHS N78D) and stripes (RHS N78C). Lower surface: Basic color: Reddish-purple (RHS N78B). Over color: Small white edge (RHS NN155C) and light reddish-purple region (RHS N78D) toward the tip. Number of spots and stripes on the dorsal sepals (upper surface): Medium stripes. Color of spots, dots, and stripes on the dorsal sepals (upper surface): RHS N78C and dots (RHS 70A). Density of netting of the dorsal sepals (upper surface): None. Color of the netting: Not applicable.

*Lateral sepals*.—Shape: Ovate. Apex: Obtuse asymmetric. Margin: Entire. Length (from base to tip): 17.0 mm to 19.0 mm. Width: 27.0 mm to 29.0 mm. Position of the broadest part of the lateral sepals: Toward the base. Color (when fully opened): Upper surface: Basic color: Light purple (RHS 76A). Over color: Light yellow-green (a color in between RHS 145C and RHS 145D) with dots (RHS 70A) at the base and stripes (RHS N78D) diluting toward the tips. Lower surface: Basic color: Reddish-purple (RHS N78B). Over color: Hint of light yellow-green (RHS 145D) at the base; reddish-purple midvein (RHS N78A) toward the tip. Number of spots, dots, and stripes on the lateral sepals (upper surface): Very few dots and few stripes. Color of spots, dots, and stripes on the lateral sepals (upper surface): Dots (RHS 70A) and stripes (RHS N78D). Density of netting of the lateral sepals (upper surface): None. Color of the netting (upper surface): Not applicable.

*Labellum* (*lip*).—Whiskers: Present. Length of whiskers: 5.0 mm to 6.0 mm. Color of whiskers: White (HRS NN155C). Pubescence on the lip: Absent.

*Lateral lobe*.—Shape: Type V (as described in the International Union for the Protection of New Varieties of Plants (UPOV) Test Guidelines for *Phalaenopsis*); spatulate. Margin: Undulated (widely wavy). Length: 14.0 mm to 16.0 mm. Width: 10.0 mm to 12.0 mm. Color: Upper surface: Light yellow (RHS 9C) and striped (RHS 187D) at the base; very light purple (RHS 76B) and yellow (RHS 14A) on one side toward the tip. Lower surface: White (RHS NN155C) with a touch of purplish-red (RHS N77B) at the base; light purple (RHS 76A) and yellow (RHS 14B) on one side toward the tip. Number of spots and stripes on the lateral lobe: Medium stripes. Color of spots and stripes on the lateral lobe: RHS 187D. Density of netting of the lateral lobe: None. Color of the netting: None.

*Apical lobe*.—Shape: Triangular. Margin: Entire. Length: 15.0 mm to 17.0 mm. Width: 15.0 mm to 17.0 mm. Color: Upper surface: Dark reddish-orange (a color in between RHS 183B and RHS 178B) at the base; yellow (RHS 13A); white (RHS NN155C) with a light purple midvein (RHS 76A) toward whiskers. Lower surface: Red margin (RHS 183B); yellow (RHS 13B) on sides; purplish-pink (RHS N78C) at the middle from base toward whiskers. Number of spots and stripes on the apical lobe: None. Color of spots and stripes on the apical lobe: Not applicable. Density of netting of the apical lobe: None. Color of the netting: None.

*Callus*.—Average size: Small. Height: 4.0 mm to 5.0 mm. Length: 4.0 mm to 5.0 mm. Width: 3.0 mm to 4.0 mm. Color: Yellow (RHS 13A); dotted (RHS 71A).

Reproductive organs:

*Column*.—Length: 8.0 mm to 10.0 mm. Diameter: 4.0 mm to 5.0 mm. Color: Very light purple (RHS 76B) with light reddish-purple tip (RHS N78D).

*Pollinia*.—Quantity: 2. Diameter: 0.7 mm to 0.9 mm. Color: Orange (RHS 24A).

*Ovary*.—Length: 7.0 mm to 9.0 mm. Diameter: 1.8 mm to 2.0 mm.

*Pedicel*.—Length: 28.0 mm to 30.0 mm. Diameter: 2.1 mm to 2.3 mm. Color: Dark red (RHS 187A) with a touch of green (RHS 146D) at the base; very light purple (RHS 76B) and purplish-pink (RHS N78C) toward the flower. Texture: Smooth.

Disease, pest, and stress resistance: No specific resistance or susceptibility observed to pathogens and pests common to *Phalaenopsis* to date.

Fruit and seeds: Fruit and seed development has not been observed on plants of the new *Phalaenopsis* to date.

COMPARISON WITH PARENTAL LINES AND MOST SIMILAR VARIETIES

'PHALWALWHO' differs from the female parent plant '8543-01' (unpatented) in that 'PHALWALWHO' has obtuse petal apexes and very light purple columns with light reddish-purple tips, whereas '8543-01' has emarginated petal apexes and white columns. Additionally, 'PHALWALWHO' has smaller flowers than '8543-01'.

The male parent plant of 'PHALWALWHO', cultivar '20370-01' (unpatented), is no longer available, therefore a meaningful comparison cannot be made.

'PHALWALWHO' is most similar to the commercial *Phalaenopsis* plants named 'PHALFUSBI' (U.S. Plant Pat. No. 30,481) and 'PHALIJBAK' (U.S. Plant Pat. No. 32,935). 'PHALWALWHO' differs from the commercial variety 'PHALFUSBI' in that 'PHALWALWHO' has white whiskers and slightly emarginated dorsal sepal apexes, whereas 'PHALFUSBI' has dark red-orange whiskers and obtuse dorsal sepal apexes. Additionally, 'PHALWALWHO' has shorter internodes and narrower leaves than 'PHALFUSBI'.

'PHALWALWHO' differs from the commercial variety 'PHALIJBAK' in that 'PHALWALWHO' has white whiskers, slightly emarginated dorsal sepal apexes, and very light purple columns with light reddish-purple tips, whereas 'PHALIJBAK' has purplish-pink whiskers, obtuse dorsal sepal apexes, and white columns with purplish-pink tips.

I claim:

1. A new and distinct variety of *Phalaenopsis* plant named 'PHALWALWHO', substantially as described and illustrated herein.

* * * * *